US00RE41341E

(19) United States
(12) Reissued Patent
Atkins et al.

(10) Patent Number: US RE41,341 E
(45) Date of Reissued Patent: May 18, 2010

(54) ESTER SYNTHESIS

(75) Inventors: Martin P. Atkins, Ashford (GB); Bhushan Sharma, Hounslow (GB)

(73) Assignee: Ineos Europe Limited (GB)

(21) Appl. No.: 11/712,545

(22) Filed: Feb. 28, 2007

Related U.S. Patent Documents

Reissue of:
(64) Patent No.: 5,861,530
Issued: Jan. 19, 1999
Appl. No.: 08/687,811
Filed: Jul. 26, 1996

(30) Foreign Application Priority Data

| | | |
|---|---|---|
| Aug. 2, 1995 | (GB) | 9515813 |
| Feb. 22, 1996 | (GB) | 9603770 |
| Jun. 25, 1996 | (GB) | 9613227 |

(51) Int. Cl.
*C07C 67/04* (2006.01)

(52) U.S. Cl. ..... 560/247
(58) Field of Classification Search ..... 560/247
See application file for complete search history.

(56) References Cited

U.S. PATENT DOCUMENTS

| | | | |
|---|---|---|---|
| 2,174,985 | A | 10/1939 | Lazier et al. |
| 5,086,031 | A | 2/1992 | Deller et al. |
| 5,241,106 | A | 8/1993 | Inoue et al. |

FOREIGN PATENT DOCUMENTS

| | | |
|---|---|---|
| EP | 0 562 139 | 12/1995 |
| EP | 0 538 826 | 1/1996 |
| EP | 0 757 027 | 7/1996 |
| EP | 0 959 064 | 12/2001 |
| GB | 1258390 | 1/1972 |
| JP | 5-301842 | 5/1993 |
| JP | 05-170698 | 7/1993 |
| JP | 05-255185 | 10/1993 |
| JP | 05-279297 | 10/1993 |
| JP | 05-301842 | 11/1993 |
| JP | 6-9454 | 1/1994 |

OTHER PUBLICATIONS

European Search Report for EP 96 30 5369.

*Primary Examiner*—Paul A Zucker
(74) *Attorney, Agent, or Firm*—Fay Sharpe LLP

(57) ABSTRACT

This invention relates to a process for the production of lower aliphatic esters by reacting a lower olefin with a saturated lower aliphatic mono-carboxylic acid in the vapor phase in the presence of a heteropolyacid catalyst characterized in that an amount of water in the range from 1–10 mole % based on the total of the olefin, aliphatic monocarboxylic acid and water is added to the reaction mixture during the reaction. The presence of water enhances the yield of the desired ester. The reaction mixture may optionally contain a di-ether to minimize the by-products.

The process is particularly suitable for producing ethyl acetate from ethylene and acetic acid in the presence of water.

26 Claims, No Drawings

ESTER SYNTHESIS

Matter enclosed in heavy brackets [ ] appears in the original patent but forms no part of this reissue specification; matter printed in italics indicates the additions made by reissue.

The present invention relates to a process for the synthesis of esters by reacting an olefin with a lower carboxylic acid in the presence of an acidic catalyst.

It is well known that olefins can be reacted with lower aliphatic carboxylic acids to form the corresponding esters. One such method is described in GB-A-1259390 in which an ethylenically unsaturated compound is contacted with a liquid medium comprising a carboxylic acid and a free heteropolyacid of molybdenum or tungsten. This process is a homogeneous process to which the heteropolyacid catalyst is unsupported. A further process for producing esters is described in JP-A-05294894 in which a lower fatty acid is esterified with a lower olefin to form a lower fatty acid ester. In this document, the esterification reaction is carried out in the gaseous phase in the presence of a catalyst consisting of at least one heteropolyacid salt of a metal e.g. Li, Cu, Mg or K, being supported on a carrier. The heteropolyacid used is phosphotungstic acid and the carrier described is silica.

It has now been found that the process efficiency can be improved significantly by co-feeding water to the reaction mixture.

Accordingly, the present invention is a process for the production of lower aliphatic esters said process comprising reacting a lower olefin with a saturated lower aliphatic mono-carboxylic acid in the vapour phase in the presence of a heteropolyacid catalyst characterised in that an amount of water in the range from 1–10 mole % based on the total of the olefin, aliphatic mono-carboxylic acid and water is added to the reaction mixture during the reaction.

A feature of the invention is the addition of water as a component of the reaction mixture. Surprisingly, it has been fond that the presence of water in the reaction mixture in an amount of 1–10 mole %, preferably from 1 to 7 mole %, e.g. 1 to 5 mole %, based on the total feed enhances the stability of the catalyst and thereby enhances the efficiency of the process. Furthermore, the presence of water also reduces the selectivity of the process to undesired by-products such as e.g. oligomers and other unknowns, excluding diethyl ether and ethanol.

It has further been found that dosing the reaction mixture with amounts of di-ether such as e.g. diethyl ether, as a co-feed also reduces the formation of undesirable by-products. The amount of di-ether co-fed is suitably in the range from 1 to 6 mole %, preferably in the range from 1 to 3 mole % based on the total reaction mixture comprising the olefin, the aliphatic carboxylic acid, water and diethyl ether. The di-ether co-fed may correspond to the by product di-ether from the reaction generated from the reactant olefin. Where a mixture of olefins is used, e.g. a mixture of ethylene and propylene, the di-ether may in turn be an unsymmetrical di-ether. The di-ether co-feed may thus be the by-product of the reaction which by-product is recycled to the reaction mixture.

The term "heteropolyacids" as used herein and throughout the specification is meant to include the free acids. The heteropolyacids used to prepare the esterification catalysts of the present invention therefore include inter alia the free acids and coordination type salts thereof in which the anion is a complex, high molecular weight entity. Typically, the anion is comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known e.g. as Keggin, Wells-Dawson and Anderson-Evans-Perloff structures.

Heteropolyacids usually have a high molecular weight e.g. in the range from 700–8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be used as the catalysts in the present invention include:

12-tungstophosphoric acid—$H_3[PW_{12}O_{40}].xH_2O$ 12-molybdophosphoric acid—$H_3[PMo_{12}O_{40}].xH_2O$ 12-tungstosilicic acid—$H_4[SiW_{12}O_{40}].xH_2O$ 12-molybdosilicic acid—$H_4[SiMo_{12}O_{40}].xH_2O$ Potassium tungstophosphate—$K_6[P_2W_{18}O_{62}].xH_2O$ Sodium molybdophosphate—$Na_3[PMo_{12}O_{40}].xH_2O$ Ammonium molybdodiphosphate—$(NH_4)_6[P_2Mo_{18}O_{62}].xH_2O$ Sodium tungstonickelate—$Na_4[NiW_6O_{24}H_6].xH_2O$ Ammonium molybdodicobaltate—$(NH_4)[Co_2Mo_{10}O_{36}].xH_2O$ Cesium hydrogen tungstosilicate—$Cs_3H[SiW_{12}O_{40}].xH_2O$ Potassium molybdodivanado phosphate—$K_5[PMoV_2O_{40}].xH_2O$ The heteropolyacid catalyst whether used as a free acid or as a salt thereof is suitably supported, preferably on a siliceous support. The siliceous support is suitably in the form of extrudates or pellets.

The siliceous support used is most preferably derived from an amorphous, non-porous synthetic silica especially fumed silica, such as those produced by flame hydrolysis of $SiCl_4$. Specific examples of such siliceous supports include Support 350 made by pelletisation of AEROSIL® 200 (both ex Degussa). This pelletisation procedure is suitably carried out by the process described in U.S. Pat. No. 5,086,031 (see especially the Examples) and is incorporated herein by reference. Such a process of pelletisation or extrusion does not involve any steam treatment steps and the porosity of the support is derived from the interstices formed during the pelletisation or extrusion step of the non-porous silica. The silica support is suitably in the form of pellets or beads or are globular in shape having an average particle diameter of 2 to 10 mm, preferably 4 to 6 mm. The siliceous support suitably has a pore volume in the range from 0.3–1.2 ml/g, preferably from 0.6–1.0 ml/g. The support suitably has a crush strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 Å preferably an average pore radius of 30 to 100 Å.

In order to achieve optimum performance, the siliceous support is suitably free of extraneous metals or elements which might adversely affect the catalytic activity of the system. The siliceous support suitably has at least 99% w/w purity, i.e. the impurities are less than 1% w/w, preferably less than 0.60% w/w and more preferably less than 0.30% w/w.

Other pelleted silica supports are the Grace 57 and 1371 grades of silica. In particular, Grace silica No. 1371 has an average bulk density of about 0.39 g/ml, an average pore volume of about 1.15 ml/g and an average particle size ranging from about 0.1–3.5 mm. These pellets can be used as such or after crushing to an average particle size in the range from 0.5–2 mm and sieving before being used as the support for the heteropolyacid catalyst.

The impregnated support is suitably prepared by dissolving the heteropolyacid, which is preferably a tungstosilicic acid, in e.g. distilled water, and then adding the support to the aqueous solution so formed. The support is suitably let to soak in the acid solution for a duration of several hours, with periodic manual stirring, after which time it is suitably filtered using a Buchner funnel in order to remove any excess acid.

The wet catalyst thus formed is then suitably placed in an oven at elevated temperature for several hours to dry, after which time it is allowed to cool to ambient temperature in a desiccator. The weight of the catalyst on drying, the weight of the support used and the weight of the acid on support was obtained by deducting the latter from the former from which the catalyst loading in g/liter was determined.

Alternatively, the support may be impregnated with the catalyst using the incipient wetness technique with simultaneous drying on a rotary evaporator.

This supported catalyst (measured by weight) can then be used in the esterification process. The amount of heteropolyacid deposited/impregnated on the support for use in the esterification reaction is suitably in the range from 10 to 60% by weight, preferably from 30 to 50% by weight based on the total weight of the heteropolyacid and the support.

In the esterification reaction, the olefin reactant used is suitably ethylene, propylene or mixtures thereof Where a mixture of olefins is used, the resultant product will inevitably a mixture of esters. The source of the olefin reactant used may be a refinery product or a chemical grade olefin which invariably contain some alkanes admixed therewith.

The saturated, lower aliphatic mono-carboxylic acid reactant is suitably a C1–C4 carboxylic acid and is preferably acetic acid.

The reaction mixture suitably comprises a molar excess of the olefin reactant with respect to the aliphatic monocarboxylic acid reactant. Thus the mole ratio of olefin to the lower carboxylic acid in the reaction mixture is suitably in the range from 1:1 to 15:1, preferably from 10:1 to 14:1.

The reaction is carried out in the vapour phase suitably above the dew point of the reactor contents comprising the reactant acid, any alcohol formed in situ, the product ester and water as stated above. The amount of water is in the range from 1–10 mole %, suitably from 1–7 mole %, preferably from 1–5 mole % based on the total amount of olefin, carboxylic acid and water. Dew point is the temperature at which condensation of a vapour of a given sample in air takes place. The dew point of any vaporous sample will depend upon its composition. The supported heteropolyacid catalyst is suitably used as a fixed bed which may be in the form of a packed column. The vapours of the reactant olefins and acids are passed over the catalyst suitably at a GHSV in the range from 100 to 5000 per hour, preferably from 300 to 2000 per hour.

The esterification reaction is suitably carried out at a temperature in the range from 150°–200° C. using a reaction pressure which is at least 400 KPa, preferably from 500–3000 Kpa depending upon the relative mole ratios of olefin to acid reactant and the amount of water used.

The water added to the reaction mixture is suitably present in the form of steam and is capable of generating a mixture of esters and alcohols in the process. The products of the reaction are recovered by e.g. fractional distillation. Where esters are produced, whether singly or as mixture of esters, these may be hydrolysed to the corresponding alcohols or mixture of alcohols in relatively high yields and purity. By using this latter technique the efficiency of the process to produce alcohols from olefins is significantly improved over the conventional process of producing alcohols by hydration of olefins.

The present invention is further illustrated with reference to the following Examples and Comparative Tests.

EXAMPLES

In all the Examples, the reaction conditions used and the results achieved are tabulated below. In these tables, the following abbreviations have been used:

| | |
|---|---|
| HOS | Hours on stream |
| Bed (T/M/B) | Bed (top/middle/bottom) |
| HAC | Acetic Acid |
| $C_2H_4$ | Ethylene |
| $H_2O$ | Water |
| EtAc | Ethyl acetate |
| EtOH | Ethanol |
| DEE | Diethyl ether |
| GHSV | Gas hourly space velocity |
| g/Lcat/h | Gram per liter of catalyst per hour |
| STP | Standard temperature & pressure |
| STY | Space time yield |

Example 1

A. Catalyst Preparations

Catalyst 1

Silica granules (Grace 1371 grade, 530 $m^2/g$, bulk density 0.39 g/ml, pore volume 1.15 ml/g, ca. 1–3 mm, 70 g, ex W R Grace) were soaked over 24 hours with intermittent stirring in a solution of silicotungstic acid [$H_4SiW_{12}O_{40}.26H_2O$] (65.53 g, ex Japan New Metals) dissolved in 250 mlo distilled water in order to impregnate the silica support with the silicophosphoric acid catalyst. After this duration, excess catalyst solution was decanted and filtered off. The resultant catalyst impregnated support was then dried in flowing nitrogen gas overnight at 120° C. The supported catalyst so formed was then left in a desiccator to cool and was finally reweighed. The resultant support catalyst had a heteropolyacid catalyst loading of 92 g/liter.

Catalyst 2: Silica granules (Grace 57 grade, surface area 510 $m^2/g$, bulk density 0.649 g/ml, pore volume 1.0267 ml/g, ca. 5–8 mm, 57.7 g, ex W R Grace) was soaked in a solution of 12-tungstosilicic acid [$H_4SiW_{12}O_{40}.26H_2O$] (ex Johnson Matthey, 69.4 dissolved in 200 ml distilled water) for 24 hours with intermittent stirring in order to impregnate the support with the catalyst. Thereafter the excess solution of the silicotungstic acid catalyst was removed by decantation and filtration. The resultant catalyst impregnated support was then dried overnight under flowing nitrogen at 120° C. The dried supported catalyst so formed was cooled in a desiccator and had a heteropolyacid catalyst loading of 190g/liter.

Catalyst 3: The above process of Catalyst 2 was repeated and was found to have a heteropolyacid catalyst loading of 192 g/liter.

B. Catalyst Forming

All the catalysts produced above were broken down and sieved to obtain the desired pellet size for loading into the esterification reactor.

C. Catalyst Testing

The reactor used was a three-zone Severn Sciences reactor constructed of Hastelloy C-276 capable of withstanding glacial acetic acid up to 300° C. and 15000 Kpa (150 barg) pressure (length 650 mm, outer diameter 22 mm, internal diameter 16 mm). It had a thermowell running the entire reactor length (5 mm outer diameter) and 1.77 cm outer diameter Swagelock VCR joints at each end. Gas from cylinders of ethylene and nitrogen were taken off at 1000 Kpa (10 barg) and then compressed to 5000–12000 Kpa (50–120 barg), via Haskel boosters, before being regulated and fed to mass-flow controllers. The liquid feed systems had 2 $dm^3$ reservoirs maintained under a nitrogen blanket of 10 KPa-80 KPa (0.1–0.8 barg).

A cooling jacket was provided to condense products in the gas stream back to liquids prior to collection in a receiver. The majority of the liquid product was collected at room temperature.

A pre-heating zone was located upstream of the catalyst bed. The pre-heating zone was separated from the catalyst bed by a plug of glass wool. Another plug of gas wool was used downstream of the catalyst bed to reduce dead volume and help maintain the catalyst bed in the centre section of the reactor.

The reaction was started up by pressurising the reactor to 1000 KPa (10 barg) with nitrogen, establishing the desired flow rate (which is the same as that used later for the olefin feed) and then increasing the reactor temperature to the desired operating conditions (170° C. or 180° C.) over a one hour period. The liquid pump for the mixture of acetic acid/water mixture was switched on initially at the desired flow rate and the olefin admitted into the reactor on liquid breakthrough at the collection pots, usually after 2 to 3 hours. The flows were then adjusted to give the desired feed molar ratios and GHSVs. The reactor effluent was collected at regular intervals. Liquid product was drained off, weighed and then analysed by GC. The gas stream was sampled downstream of the liquid collection points and also analysed by GC. Total gas out during a test period was measured using a wet-gas meter.

The above process/catalysts were used to esterify ethylene with acetic acid. The relative amounts of each of the Catalysts 1 to 3 used, their bed size and bed length in performing the esterification reaction were as follows:

| Parameter | Catalyst 1 | Catalyst 2 | Catalyst 3 |
|---|---|---|---|
| Volume ($cm^3$) | 25 | 25 | 25 |
| Weight (g) | 11.3 (11.4*) | 12 | 12 |
| Pellet size (mm) | 1-2 (0.5-1*) | 0.5-1 | 0.5-1 |
| Bed length | 8.75 (14*) | 14 | 14 |

*Parameters of Catalyst 1 used for the Runs in Table 2

TABLE 1

Run Conditions: (1 Mole % Water added to feed) using Catalyst 1:

| Parameters | Run No. 1 | Run No. 2 | Run No. 3* |
|---|---|---|---|
| HOS | 17-20 | 42-45 | 70-73 (21-24) |
| Temperature (° C.) | | | |
| Applied | 170 | 170 | 170 |
| Bed (T/M/B) | 173/—/170 | 172.5/—/169.5 | 173/—/168 |
| Pressure (Kpa) | 1000 | 1000 | 1000 |
| Total feed GHSV/h (@ STP) | 980 | 980 | 974 |
| $C_2H_4$ GHSV/h | 905 | 905 | 905 |
| HAC GHSV/h | 66 | 66 | 69 |
| $H_2O$ GHSV/h | 9 | 9 | 9 |
| $C_2H_4$ (g/Lcat/h) | 1131 | 1131 | 1131 |
| HAC (g/Lcat/h) | 177 | 177 | 185 |
| $H_2O$ (g/Lcat/h) | 8 | 8 | 0 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.9/14.1/0 |
| $C_2H_4$/HAC/$H_2O$ wt % ratio | 85.9/13.5/0.6 | 85.9/13.5/0.6 | 85.9/14.1/0 |
| $C_2H_4$/HAC mole ratio | 13.7 | 13.7 | 13.1 |

*No added water used in this comparative test (not according to the invention)

Product Analysis

| Products/Analysis | Run No. 1 | Run No. 2 | Run No. 3* |
|---|---|---|---|
| HAC Conversion | 66 | 64 | 27 |
| Product Selectivity (wt %) | | | |
| EtAc | 97.3 | 97.8 | 91.6 |
| EtOH | 0.4 | 0.3 | 0.1 |
| DEE | 1.8 | 1.3 | 0.0 |
| Acetaldehyde | 0.0 | 0.0 | 0.0 |
| Oligomers | 0.3 | 0.6 | 1.4 |
| Others | 0.1 | 0.04 | 6.8 |
| EtAc Yield | 95 | 59 | 25 |
| EtAc STY (g/Lcat/h) | 180 | 160 | 44 |
| Carbon Balance (mol %) | 104 | 105 | 100 |
| Oxygen Balance (mol %) | 95 | 102 | 81 |
| Mass Balance | 103 | 105 | 99 |
| Water recovered (%) | 69 | 73 | — |

*No water used and is hence a comparative test (not according to the invention)

TABLE 2

| Parameters | Run No. 4 | Run No. 5 | Run No. 6 | Run No. 7 |
|---|---|---|---|---|
| Run Conditions: (1 Mole % Water added to feed) using Catalyst 1: | | | | |
| HOS | 19-22 | 44-77 | 68.75-73.75 | 91-94 |
| Temperature (° C.) | | | | |
| Applied | 180 | 180 | 180 | 180 |
| Bed (T/M/B) | 181.5/186/182.5 | 181.5/185/183 | 181.3/184.5/181.2 | 181.4/184/181.1 |
| Pressure (Kpa) | 1000 | 1000 | 1000 | 1000 |
| Total feed GHSV/h (@ STP) | 980 | 980 | 980 | 980 |
| $C_2H_4$ GHSV/h | 905 | 905 | 905 | 905 |
| HAC GHSV/h | 66 | 66 | 66 | 66 |
| $H_2O$ GHSV/h | 9 | 9 | 9 | 9 |
| $C_2H_4$ (g/Lcat/h) | 1131 | 1131 | 1131 | 1131 |
| HAC (g/Lcat/h) | 177 | 177 | 177 | 177 |
| $H_2O$ (g/Lcat/h) | 8 | 8 | 8 | 8 |
| Feed contact time [1/GHSV](secs) | 4 | 4 | 4 | 4 |
| $C_2H_4$/HAC/$H_2O$ mole % ratio | 92.3/6.7/1.0 | 92.3/6.7/1.0 | 92.3/6.7/1.0 | 92.3/6.7/1.0 |
| $C_2H_4$/HAC/$H_2O$ wt % ratio | 86/13.4/0.6 | 86/13.4/0.6 | 86/13.4/0.6 | 86/13.4/0.6 |
| $C_2H_4$/HAC mole ratio | 13.7 | 13.7 | 13.7 | 13.7 |
| Product Analysis | | | | |
| Products/Analysis | Run No. 4 | Run No. 5 | Run No. 6 | Run No. 7 |
| Ethylene conversion (%) | 5.3 | 3.9 | 4.1 | 6.0 |
| HAC Conversion | 71 | 64 | 60 | 54 |
| Product Selectivity (wt %) | | | | |
| EtAc | 95.9 | 97.2 | 97.8 | 98.1 |
| EtOH | 0.7 | 0.6 | 0.5 | 0.6 |
| DEE | 2.3 | 1.8 | 1.3 | 1.0 |
| Acetaldehyde | 0.0 | 0.0 | 0.0 | 0.0 |
| Oligomers | 0.8 | 0.3 | 0.6 | 0.2 |
| Others | 0.3 | 0.1 | 0.0 | 0.0 |
| EtAc Yield | 68 | 63 | 59 | 53 |
| EtAc STY (g/Lcat/h) | 194 | 183 | 164 | 148 |
| Carbon Balance (mol %) | 100 | 199 | 100 | 97 |
| Oxygen Balance (mol %) | 94 | 89 | 93 | 88 |
| Mass Balance | 100 | 99 | 99 | 96 |
| Water recovered (%) | 53 | 56 | 62 | 65 |

TABLE 3

| Parameters | Run No. 8 | Run No. 9 | Run No. 10 |
|---|---|---|---|
| Run Conditions: (1 Mole % Water added to feed) using Catalyst 2: | | | |
| HOS | 14.75-17.5 | 38.5-41.5 | 62.5-65.5 |
| Temperature (° C.) | | | |
| Applied | 180 | 180 | 180 |
| Bed (T/M/B) | 179.5/189/182.8 | 179.6/187.5/182.9 | 179.4/186.5/182.8 |
| Pressure (Kpa) | 1000 | 1000 | 1000 |
| Total feed GHSV/h (@ STP) | 981 | 981 | 981 |
| $C_2H_4$ GHSV/h | 905 | 905 | 905 |
| HAC GHSV/h | 66 | 66 | 66 |
| $H_2O$ GHSV/h | 10 | 10 | 10 |
| $C_2H_4$ (g/Lcat/h) | 1131 | 1131 | 1131 |
| HAC (g/Lcat/h) | 177 | 177 | 177 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.9/6.7/1.0 |
| $C_2H_4$/HAC/$H_2O$ wt % ratio | 85.9/13.5/0.6 | 85.9/13.5/0.6 | 85.9/13.5/0.6 |
| $C_2H_4$/HAC mole ratio | 13.7 | 13.7 | 13.7 |

TABLE 3-continued

| Products/Analysis | Run No. 8 | Run No. 9 | Run No. 10 |
|---|---|---|---|
| Product Analysis | | | |
| Ethylene Conversion | 7.3 | 3.9 | 3.3 |
| HAC Conversion | 81 | 77 | 75 |
| Product Selectivity (wt %) | | | |
| EtAc | 92.7 | 95.2 | 96.0 |
| EtOH | 0.8 | 0.7 | 0.7 |
| DEE | 3.8 | 2.8 | 2.2 |
| Acetaldehyde | 0.0 | 0.0 | 0.0 |
| Oligomers | 1.6 | 0.9 | 0.8 |
| Others | 1.1 | 0.5 | 0.3 |
| EtAc Yield | 75 | 73 | 72 |
| EtAc STY (g/Lcat/h) | 213 | 211 | 201 |
| Carbon Balance (mol %) | 100 | 102 | 103 |
| Oxygen Balance (mol %) | 99 | 96 | 98 |
| Mass Balance | 100 | 102 | 103 |
| Water recovered (%) | 45 | 43 | 51 |

TABLE 4

| Run Conditions: (5 Mole % Water added to feed) using Catalyst 2: | | | |
|---|---|---|---|
| Parameters | Run No. 11 | Run No. 12 | Run No. 13 |
| HOS | 90.5-95.5 | 134.5-137.5 | 158.5-161.5 |
| Temperature (° C.) | | | |
| Applied | 180 | 180 | 180 |
| Bed (T/M/B) | 179.3/188.5/ 182.4 | 179.6/188.5/ 183.4 | 179.5/188.5/ 183.4 |
| Pressure (Kpa) | 1000 | 1000 | 1000 |
| Total feed GHSV/h (@ STP) | 975 | 975 | 975 |
| $C_2H_4$ GHSV/h | 866 | 866 | 866 |
| HAC GHSV/h | 61 | 61 | 61 |
| $H_2O$ GHSV/h | 48 | 48 | 48 |
| $C_2H_4$ (g/Lcat/h) | 1083 | 1083 | 1083 |
| HAC (g/Lcat/h) | 164 | 164 | 164 |
| $H_2O$ (g/Lcat/h) | 38 | 38 | 38 |
| Feed contact time [1/GHSV](secs) | 4 | 4 | 4 |
| $C_2H_4$/HAC/$H_2O$ mole % ratio | 88.8/6.3/4.9 | 88.8/6.3/4.9 | 88.8/6.3/4.9 |
| $C_2H_4$/HAC/$H_2O$ wt % ratio | 84.2/12.8/3 | 84.2/12.8/3 | 84.2/12.8/3 |
| $C_2H_4$/HAC mole ratio | 14.2 | 14.2 | 14.2 |
| Product Analysis | | | |
| Products/Analysis | Run No. 11 | Run No. 12 | Run No. 13 |
| Ethylene Conversion | 4.4 | 4.0 | 4.3 |
| HAC Conversion | 68 | 72 | 72 |
| Product Selectivity (wt %) | | | |
| EtAc | 85.2 | 82.9 | 82.0 |
| EtOH | 3.7 | 3.7 | 3.9 |
| DEE | 10.5 | 13.0 | 13.6 |
| Acetaldehyde | 0.0 | 0.0 | 0.0 |
| Oligomers | 0.6 | 0.4 | 0.5 |
| Others | 0.01 | 0.02 | 0.07 |
| EtAc Yield | 58 | 60 | 59 |
| EtAc STY (g/Lcat/h) | 203 | 215 | 210 |
| Carbon Balance (mol %) | 102 | 103 | 103 |
| Oxygen Balance (mol %) | 87 | 87 | 89 |
| Mass Balance | 101 | 102 | 102 |
| Water recovered (%) | 43 | 39 | 42 |

TABLE 5

| Run Conditions: (5 Mole % Water added to feed) using Catalyst 3: | | | |
|---|---|---|---|
| Parameters | Run No. 14 | Run No. 15 | Run No. 16 |
| HOS | 16-19 | 40-43 | 112.5-115.5 |
| Temperature (° C.) | | | |
| Applied | 180 | 180 | 180 |
| Bed (T/M/B) | 179.1/191/ 183.2 | 179.1/190.5/ 183.5 | 179.2/190/ 183.8 |
| Pressure (Kpa) | 1000 | 1000 | 1000 |
| Total feed GHSV/h (@ STP) | 980 | 980 | 980 |
| $C_2H_4$ GHSV/h | 866 | 866 | 866 |
| HAC GHSV/h | 64 | 64 | 64 |
| $H_2O$ GHSV/h | 50 | 50 | 50 |
| $C_2H_4$ (g/Lcat/h) | 1083 | 1083 | 1083 |
| HAC (g/Lcat/h) | 170 | 170 | 170 |
| $H_2O$ (g/Lcat/h) | 40 | 40 | 40 |
| Feed contact time [1/GHSV](secs) | 4 | 4 | 4 |
| $C_2H_4$/HAC/$H_2O$ mole % ratio | 88.4/6.5/5.1 | 88.4/6.5/5.1 | 92.3/6.7/1.0 |
| $C_2H_4$/HAC/$H_2O$ wt % ratio | 83.7/13.2/3.1 | 83.7/13.2/3.1 | 86/13.4/0.6 |
| $C_2H_4$/HAC mole ratio | 13.6 | 13.6 | 13.6 |

TABLE 5-continued

| Product Analysis | | | |
|---|---|---|---|
| Products/Analysis | Run No. 14 | Run No. 15 | Run No. 16 |
| Ethylene Conversion | 6.6 | 7.6 | 6.3 |
| HAC Conversion | 86 | 85 | 83 |
| Product Selectivity (wt %) | | | |
| EtAc | 73.4 | 74.0 | 73.2 |
| EtOH | 3.7 | 3.7 | 3.5 |
| DEE | 22.0 | 21.5 | 22.9 |
| Acetaldehyde | 0.0 | 0.0 | 0.0 |
| Oligomers | 0.6 | 0.7 | 0.5 |
| Others | 0.2 | 0.1 | 0.0 |
| EtAc Yield | 63 | 63 | 60 |
| EtAc STY (g/Lcat/h) | 219 | 221 | 224 |
| Carbon Balance (mol %) | 106 | 104 | 105 |
| Oxygen Balance (mol %) | 103 | 101 | 95 |
| Mass Balance | 105 | 104 | 104 |
| Water recovered (%) | 40 | 40 | 36 |

TABLE 6

| Run Conditions: (5 Mole % Water added to feed) using Catalyst 3: | | | |
|---|---|---|---|
| Parameters | Run No. 17 | Run No. 18 | Run No. 19 |
| HOS | 160.5-163.5 | 208.5-211.5 | 285.5-288.5 |
| Temperature (° C.) | | | |
| Applied | 180 | 180 | 180 |
| Bed (T/M/B) | 179.2/190/ 184.1 | 179.3/190/ 184.3 | 179.3/190/ 184.2 |
| Pressure (Kpa) | 1000 | 1000 | 1000 |
| Total feed GHSV/h (@ STP) | 980 | 980 | 980 |
| $C_2H_4$ GHSV/h | 866 | 866 | 866 |
| HAC GHSV/h | 64 | 64 | 64 |
| $H_2O$ GHSV/h | 50 | 50 | 50 |
| $C_2H_4$ (g/Lcat/h) | 1083 | 1083 | 1083 |
| HAC (g/Lcat/h) | 170 | 170 | 170 |
| $H_2O$ (g/Lcat/h) | 40 | 40 | 40 |
| Feed contact time [1/GHSV](secs) | 4 | 4 | 4 |
| $C_2H_4$/HAC/$H_2O$ mole % ratio | 88.4/6.5/5.1 | 88.4/6.5/5.1 | 88.4/6.5/5.1 |
| $C_2H_4$/HAC/$H_2O$ wt % ratio | 83.7/13.2/3.1 | 83.7/13.2/3.1 | 83.7/13.2/3.1 |
| $C_2H_4$/HAC mole ratio | 13.6 | 13.6 | 13.6 |
| Product Analysis | | | |
| Products/Analysis | Run No. 17 | Run No. 18 | Run No. 19 |
| Ethylene Conversion | 8.8 | 8.7 | 8.4 |
| HAC Conversion | 85 | 86 | 88 |
| Product Selectivity (wt %) | | | |
| EtAc | 73.2 | 73.0 | 73.7 |
| EtOH | 3.6 | 3.9 | 3.7 |
| DEE | 22.6 | 22.6 | 22.1 |
| Acetaldehyde | 0.0 | 0.0 | 0.0 |
| Oligomers | 0.5 | 0.5 | 0.5 |
| Others | 0.1 | 0.1 | 0.1 |
| EtAc Yield | 62 | 63 | 65 |
| EtAc STY (g/Lcat/h) | 217 | 217 | 225 |
| Carbon Balance (mol %) | 104 | 104 | 104 |
| Oxygen Balance (mol %) | 103 | 103 | 103 |
| Mass Balance | 103 | 104 | 104 |
| Water recovered (%) | 40 | 41 | 38 |

TABLE 7

| Run Conditions: (5 Mole % Water added to feed) using Catalyst 3: | | | |
|---|---|---|---|
| Parameters | Run No. 20 | Run No. 21* | Run No. 22* |
| HOS | 375.5-378.5 | 448.5-451.5 | 472.5-475.5 |
| Temperature (° C.) | | | |
| Applied | 180 | 180 | 180 |
| Bed (T/M/B) | 179.3/190/184.4 | 179.3/186.5/183.4 | 179.3/186.5/183.4 |
| Pressure (Kpa) | 1000 | 1000 | 1000 |
| Total feed GHSV/h (@ STP) | 980 | 1001 | 1001 |
| $C_2H_4$ GHSV/h | 866 | 866 | 866 |
| HAC GHSV/h | 64 | 64 | 64 |
| $H_2O$ GHSV/h | 50 | 50 | 50 |
| DEE GHSV/h | 0 | 21 | 21 |
| $C_2H_4$ (g/Lcat/h) | 1083 | 1083 | 1083 |
| HAC (g/Lcat/h) | 170 | 170 | 170 |
| $H_2O$ (g/Lcat/h) | 40 | 40 | 40 |
| DEE (g/Lcat/h) | 0 | 71 | 71 |
| Feed contact time [1/GHSV](secs) | 3.7 | 3.6 | 3.6 |
| $C_2H_4$/HAC/$H_2O$/DEE mole % ratio | 88.4/6.5/5.1§ | 86.5/6.4/2.1§ | 86.5/6.4/5/2.1 |
| $C_2H_4$/HAC/$H_2O$/DEE wt % ratio | 83.7/13.2/3.1§ | 79.4/12.5/2.9/5.2 | 79.4/12.5/2.9/5.2 |
| $C_2H_4$/HAC mole ratio | 13.6 | 13.6 | 13.6 |

Product Analysis

| Products/Analysis | Run No. 20 | Run No. 21 | Run No. 22 |
|---|---|---|---|
| Ethylene Conversion | 8.7 | 2.7 | 2.4 |
| HAC Conversion | 85 | 81 | 80 |
| Product Selectivity (wt %) | | | |
| EtAc | 74.1 | 71.9 | 70.8 |
| EtOH | 3.6 | 5.0 | 5.4 |
| DEE | 21.6 | 22.9 | 23.3 |
| Acetaldehyde | 0.0 | 0.0 | 0.0 |
| Oligomers | 0.5 | 0.2 | 0.5 |
| Others | 0.1 | 0.0 | 0.0 |
| EtAc Yield | 63 | 59 | 57 |
| EtAc STY (g/Lcat/h) | 226 | 226 | 222 |
| Carbon Balance (mol %) | 103 | 105 | 105 |
| Oxygen Balance (mol %) | 98 | 101 | 98 |
| Mass Balance | 102 | 105 | 104 |
| Water recovered (%) | 38 | 60 | 63 |

*co-fed additionally with 2 Mole % DEE.
§No diethyl ether used in this Run

TABLE 8

| Run Conditions: (5 Mole % Water + 2 Mole % DEE added to feed) using Catalyst 3: | | |
|---|---|---|
| Parameters | Run No. 23 | Run No. 24 |
| HOS | 479.5-500.5 | 544.5-547.5 |
| Temperature (° C.) | | |
| Applied | 180 | 180 |
| Bed (T/M/B) | 179.3/186.5/183.4 | 179.4/187/183.4 |
| Pressure (Kpa) | 1000 | 1000 |
| Total feed GHSV/h (@ STP) | 1001 | 1001 |
| $C_2H_4$ GHSV/h | 866 | 866 |
| HAC GHSV/h | 64 | 64 |
| $H_2O$ GHSV/h | 50 | 50 |
| DEE GHSV/h | 21 | 21 |
| $C_2H_4$ (g/Lcat/h) | 1083 | 1083 |

TABLE 8-continued

| | Run No. 23 | Run No. 24 |
|---|---|---|
| HAC (g/Lcat/h) | 170 | 170 |
| $H_2O$ (g/Lcat/h) | 40 | 40 |
| DEE (g/Lcat/h) | 71 | 71 |
| Feed contact time [1/GHSV](secs) | 3.6 | 3.6 |
| $C_2H_4$/HAC/$H_2O$/DEE mole % ratio | 86.5/6.4/5/2.1 | 86.5/6.4/5/2.1 |
| $C_2H_4$/HAC/$H_2O$/DEE wt % ratio | 79.4/12.5/2.9/5.2 | 79.4/12.5/2.9/5.2 |
| $C_2H_4$/HAC mole ratio | 13.6 | 13.6 |
| Product Analysis | | |
| Products/Analysis | | |
| Ethylene Conversion | 1.4 | 1.3 |
| HAC Conversion | 84 | 82 |
| Product Selectivity (wt %) | | |
| EtAc | 70.6 | 71.1 |
| EtOH | 5.1 | 5.2 |
| DEE | 23.9 | 23.5 |
| Acetaldehyde | 0.0 | 0.0 |
| Oligomers | 0.3 | 0.3 |
| Others | 0.0 | 0.0 |
| EtAc Yield | 59 | 58 |
| EtAc STY (g/Lcat/h) | 226 | 224 |
| Carbon Balance (mol %) | 107 | 106 |
| Oxygen Balance (mol %) | 103 | 99 |
| Mass Balance | 106 | 105 |
| Water recovered (%) | 61 | 63 |

TABLE 9

LIQUID PRODUCT DATA
GCMS
180° C., 1000 Kpa (10 barg), ethylene/acetic acid = 14

| | Run No. | | |
|---|---|---|---|
| Organics (% by Wt) | 7 | 17 | 23 |
| Water (mole % in feed) | 1 | 5 | 5 (+2% DEE) |
| Acetic acid (unreacted feed) | 52.3 | 21.2 | 16.3 |
| Ethyl acetate | 46.5 | 67.3 | 69 |
| Diethylether | 0.05 | 3 | 3.3 |
| Ethanol | 0.65 | 7.8 | 11 |
| Acetaldehyde | 0.002 | 0.04 | 0.009 |
| C6 oligomers | 0.0015 | 0 | 0 |
| C8 oligomers | 0.0055 | 0 | 0 |
| Miscellaneous oxygenates | 0.0065 | 0 | 0 |
| Aromatic hydrocarbons | 0.045 | 0 | 0 |
| Unknowns | 0.11 | 0.01 | 0 |
| BALANCE: others (Hydrocarbons & oxy compounds) | | | |

Example 2

Catalyst Preparations

Catalyst 4. 12-Tungstophosphoric acid [$H_3PW_{12}O_{40}.24H_2O$] (175 g) was dissolved in distilled water (250 ml). Lithium nitrate [$LiNO_3.2H_2O$] (0.652 g) was dissolved in distilled water (~5 ml). The lithium nitrate solution was added dropwise to the tungstophosphoric acid solution to form Solution "A".

Solution "A" was added to pelleted silica support (Grace 1371 grade, 1–3 mm, 99.5 g, ex W R Grace) and left to soak over 24 hours with occasional stirring in order to impregnate the silica with the tungstophosphoric acid catalyst. After this duration, excess solution "A" was decanted and filtered off. The resultant catalyst impregnated support was then dried in flowing nitrogen gas initially at 150° C. for 3 hours and then raised to 200° C. and maintained at that temperature for 5 hours. The supported catalyst so formed was then left in a desiccator to cool and was finally reweighed. The resultant supported catalyst had a final weight of 164.4 g, a net catalyst loading of 64.9 g and had the formula $Li_{0.1}H_{2.9}PW_{12}O_{40}.24H_2O/SiO_2$ corresponding to a loading of 255 g/l.

Catalyst 4. Pelleted silica support (Grace 1371 grade, 1–3 mm, 70 g, ex W R Grace) was soaked in a solution (250 ml) of 12-tungstosilicic acid [$H_4SiW_{12}O_{40}.26H_2O$] (65.53 g in distilled water) for 24 hours with intermittent stirring in order to impregnate the support with the catalyst. Thereafter the excess solution of the tungstosilicic acid was removed by decantation and filtration. The resultant catalyst impregnated support was then dried overnight under flowing nitrogen at 120° C. The dried supported catalyst so formed was cooled in a desiccator and had a final weight of 86.2 g, a net catalyst loading of 16.2 g and had the formula $H_4SiW_{12}O_{40}.26H_2O/SiO_2$ corresponding to a loading of 92 g/l.

The above catalysts were used to esterify ethylene with acetic acid. The relative amounts of each of these catalysts used, their bed size and bed length in performing the esterification reaction were as follows:

| Parameter | Catalyst 4 | Catalyst 5 |
|---|---|---|
| Volume ($cm^3$) | 25 | 25 |
| Weight (g) | 15.5 | 11.2-11.4 |
| Pellet size (mm) | 1-2 | 1-2 (Table 11) & 0.5-1 (Tables 12, 13 and 14) |
| Bed length | 8.5 | 8.75 |

TABLE 10

| | Run No. 25 | Run No. 26 | Run No. 27 |
|---|---|---|---|
| | (Catalyst 4-15.5 g) Run Conditions: | | |
| Parameters | | | |
| HOS | 1-3 | 19-21 | 25-27 |
| Temperature (° C.) | | | |
| Applied | 170 | 170 | 170 |
| Bed (T/M/B) | 173.5/—/170.5 | 172/—/169 | 172/—/169 |
| Pressure (Kpa) | 1000 | 1000 | 1000 |
| Total feed GHSV/h (@ STP) | 979 | 979 | 979 |
| $C_2H_4$ GHSV/h | 905 | 905 | 905 |
| HAC GHSV/h | 65 | 65 | 65 |
| $H_2O$ GHSV/h | 9 | 9 | 9 |
| $C_2H_4$ (g/Lcat/h) | 1131 | 1131 | 1131 |
| HAC (g/Lcat/h) | 173 | 173 | 173 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.4/6.6/1.0 | 92.4/6.6/1.0 | 92.4/6.6/1.0 |
| $C_2H_4$/HAC/$H_2O$ wt % ratio | 86.2/13.2/0.6 | 86.2/13.2/0.6 | 86.2/13.2/0.6 |
| $C_2H_4$/HAC mole ratio | 14.0 | 14.0 | 14.0 |
| | Product Analysis (Table 10 continued) | | |
| Products/Analysis | | | |
| HAC Conversion | 51 | 47 | 45 |
| Product Selectivity (wt %) | | | |
| EtAc | 89.7 | 98.0 | 97.7 |
| EtOH | 0.5 | 0.5 | 0.4 |

TABLE 10-continued

| | Run No. 25 | Run No. 26 | Run No. 27 |
|---|---|---|---|
| DEE | 0.9 | 0.7 | 1.0 |
| Acetaldehyde | 0.0 | 0.0 | 0.0 |
| Oligomers | 7.0 | 0.4 | 0.7 |
| Others | 1.90 | 0.49 | 0.26 |
| EtAc Yield | 45 | 46 | 44 |
| EtAc STY (g/Lcat/h) | 128 | 122 | 118 |
| Carbon Balance (mol %) | 102 | 102 | 105 |
| Oxygen Balance (mol %) | 86 | 89 | 100 |
| Mass Balance | 101 | 101 | 104 |
| Water recovered (%) | 90 | 70 | 81 |

TABLE 11

| | Run No. 28 | Run No. 29 | Run No. 30 |
|---|---|---|---|
| | (Catalyst 5-11.3 g) Run Conditions: | | |
| Parameters | | | |
| HOS | 1-2 | 17-20 | 21-24 |
| Temperature (° C.) | | | |
| Applied | 170 | 170 | 170 |
| Bed (T/M/B) | 176/—/174 | 173/—/170 | 173/—/170 |
| Pressure (Kpa) | 1000 | 1000 | 1000 |
| Total feed GHSV/h (@ STP) | 980 | 980 | 980 |
| $C_2H_4$ GHSV/h | 905 | 905 | 905 |
| HAC GHSV/h | 66 | 66 | 66 |
| $H_2O$ GHSV/h | 9 | 9 | 9 |
| $C_2H_4$ (g/Lcat/h) | 1131 | 1131 | 1131 |
| HAC (g/Lcat/h) | 177 | 177 | 177 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.4/6.6/1.0 |
| $C_2H_4$/HAC/$H_2O$ wt % ratio | 85.9/13.5/0.6 | 85.9/13.5/0.6 | 86.2/13.2/0.6 |
| $C_2H_4$/HAC mole ratio | 13.7 | 13.7 | 13.7 |
| | Product Analysis: | | |
| Products/Analysis | | | |
| HAC Conversion | 62 | 66 | 64 |
| Product Selectivity (wt %) | | | |
| EtAc | 86.0 | 97.3 | 97.6 |
| EtOH | 2.4 | 0.4 | 0.4 |
| DEE | 3.3 | 1.8 | 1.4 |
| Acetaldehyde | 0.0 | 0.0 | 0.0 |
| Oligomers | 2.4 | 0.3 | 0.6 |
| Others | 5.9 | 0.1 | 0.1 |
| EtAc Yield | 53 | 65 | 62 |
| EtAc STY (g/Lcat/h) | 151 | 180 | 171 |
| Carbon Balance (mol %) | 101 | 104 | 105 |
| Oxygen Balance (mol %) | 98 | 95 | 99 |
| Mass Balance | 101 | 103 | 105 |
| Water recovered (%) | 70 | 69 | 67 |

TABLE 12

| | Run No. 31 | Run No. 32 | Run No. 33 |
|---|---|---|---|
| | (Catalyst 5-11.2 g) Run Conditions: | | |
| Parameters | | | |
| HOS | 19.25-22.5 | 23-26 | 43.25-46.25 |
| Temperature (° C.) | | | |
| Applied | 170 | 170 | 180 |
| Bed (T/M/B) | 172.5/176/— | 172.5/175.5/— | 182/187/— |
| Pressure (Kpa) | 1000 | 1000 | 1000 |

TABLE 12-continued

| | Run No. 31 | Run No. 32 | Run No. 33 |
|---|---|---|---|
| Total feed GHSV/h (@ STP) | 980 | 980 | 980 |
| $C_2H_4$ GHSV/h | 905 | 905 | 905 |
| HAC GHSV/h | 66 | 66 | 66 |
| $H_2O$ GHSV/h | 9 | 9 | 9 |
| $C_2H_4$ (g/Lcat/h) | 1131 | 1131 | 1131 |
| HAC (g/Lcat/h) | 177 | 177 | 177 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.3/6.7/1.0 |
| $C_2H_4$/HAC/$H_2O$ wt % ratio | 86/13.4/0.6 | 86/13.4/0.6 | 86/13.4/0.6 |
| $C_2H_4$/HAC mole ratio | 13.7 | 13.7 | 13.7 |
| Product Analysis: | | | |
| Products/Analysis | | | |
| HAC Conversion | 72 | 72 | 72 |
| Product Selectivity (wt %) | | | |
| EtAc | 96.0 | 94.4 | 94.9 |
| EtOH | 0.5 | 0.5 | 0.7 |
| DEE | 2.9 | 2.7 | 3.3 |
| Acetaldehyde | 0.0 | 0.0 | 0.0 |
| Oligomers | 0.4 | 1.6 | 0.7 |
| Others | 0.2 | 0.3 | 0.8 |
| EtAc Yield | 69 | 68 | 78 |
| EtAc STY (g/Lcat/h) | 203 | 194 | 210 |
| Carbon Balance (mol %) | 101 | 103 | 108 |
| Oxygen Balance (mol %) | 91 | 97 | 104 |
| Mass Balance | 100 | 103 | 108 |
| Water recovered (%) | 47 | 48 | 48 |

TABLE 13

| | Run No. 34 | Run No. 35 | Run No. 36 |
|---|---|---|---|
| (Catalyst 5-11.2 g) Run Conditions: | | | |
| Parameters | | | |
| HOS | 47-50 | 67.25-70.25 | 71-74 |
| Temperature (° C.) | | | |
| Applied | 180 | 190 | 190 |
| Bed (T/M/B) | 181.5/186.5/— | 191.5/196/— | 191.5/195.5/— |
| Pressure (Kpa) | 1000 | 1000 | 1000 |
| Total feed GHSV/h (@ STP) | 980 | 980 | 980 |
| $C_2H_4$ GHSV/h | 905 | 905 | 905 |
| HAC GHSV/h | 66 | 66 | 66 |
| $H_2O$ GHSV/h | 9 | 9 | 9 |
| $C_2H_4$ (g/Lcat/h) | 1131 | 1131 | 1131 |
| HAC (g/Lcat/h) | 177 | 177 | 177 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.3/6.7/1.0 |
| $C_2H_4$/HAC/$H_2O$ wt % ratio | 86/13.4/0.6 | 86/13.4/0.6 | 86/13.4/0.6 |
| $C_2H_4$/HAC mole ratio | 13.7 | 13.7 | 13.7 |
| Product Analysis: | | | |
| Products/Analysis | | | |
| HAC Conversion | 79 | 74 | 72 |
| Product Selectivity (wt %) | | | |
| EtAc | 95.2 | 94.7 | 94.9 |
| EtOH | 0.7 | 0.7 | 0.7 |
| DEE | 3.2 | 2.8 | 2.2 |
| Acetaldehyde | 0.0 | 0.0 | 0.0 |

TABLE 13-continued

| | Run No. 34 | Run No. 35 | Run No. 36 |
|---|---|---|---|
| Oligomers | 0.6 | 1.4 | 1.3 |
| Others | 0.2 | 0.3 | 0.8 |
| EtAc Yield | 75 | 70 | 68 |
| EtAc STY (g/Lcat/h) | 206 | 202 | 191 |
| Carbon Balance (mol %) | 105 | 102 | 104 |
| Oxygen Balance (mol %) | 102 | 94 | 99 |
| Mass Balance | 105 | 102 | 104 |
| Water recovered (%) | 47 | 52 | 54 |

TABLE 14

| | Run No. 37 | Run No. 38 | Run No. 39 |
|---|---|---|---|
| (Catalyst 5-11.4 g) Run Conditions: | | | |
| Parameters | | | |
| HOS | 19-22 | 44-47 | 68.75-71.75 |
| Temperature (° C.) | | | |
| Applied | 180 | 180 | 180 |
| Bed (T/M/B) | 181.5/186/182.5 | 181.5/185/182 | 181.3/184.5/181.2 |
| Pressure (Kpa) | 1000 | 1000 | 1000 |
| Total feed GHSV/h (@ STP) | 980 | 980 | 980 |
| $C_2H_4$ GHSV/h | 905 | 905 | 905 |
| HAC GHSV/h | 66 | 66 | 66 |
| $H_2O$ GHSV/h | 9 | 9 | 9 |
| $C_2H_4$ (g/Lcat/h) | 1131 | 1131 | 1131 |
| HAC (g/Lcat/h) | 177 | 177 | 177 |
| $H_2O$ (g/Lcat/h) | 8 | 8 | 8 |
| Feed contact time [1/GHSV](secs) | 4 | 4 | 4 |
| $C_2H_4$/HAC/$H_2O$ mole % ratio | 92.3/6.7/1.0 | 92.3/6.7/1.0 | 92.3/6.7/1.0 |
| $C_2H_4$/HAC/$H_2O$ wt % ratio | 86/13.4/0.6 | 86/13.4/0.6 | 86/13.4/0.6 |
| $C_2H_4$/HAC mole ratio | 13.7 | 13.7 | 13.7 |
| Product Analysis: | | | |
| Products/Analysis | | | |
| HAC Conversion | 71 | 64 | 60 |
| Product Selectivity (wt %) | | | |
| EtAc | 95.9 | 97.2 | 97.8 |
| EtOH | 0.7 | 0.6 | 0.5 |
| DEE | 2.3 | 1.8 | 1.3 |
| Acetaldehyde | 0.0 | 0.0 | 0.0 |
| Oligomers | 0.8 | 0.3 | 0.3 |
| Others | 0.3 | 0.1 | 0.0 |
| EtAc Yield | 68 | 63 | 59 |
| EtAc STY (g/Lcat/h) | 194 | 183 | 164 |
| Carbon Balance (mol %) | 100 | 100 | 100 |
| Oxygen Balance (mol %) | 94 | 89 | 93 |
| Mass Balance | 100 | 99 | 99 |
| Water recovered (%) | 53 | 56 | 62 |

We claim:

1. A process for the production of lower aliphatic esters said process comprising reacting a lower olefin *and a di-ether* with a saturated lower aliphatic monocarboxylic acid in the vapour phase in the presence of a free acid silico-tungstic heteropolyacid catalyst supported on a siliceous support characterized in that an amount of water in the range from 1–10 mole % based on the total of the olefin, aliphatic mono-carboxylic acid and water is added to the reaction mixture during the reaction *and the amount of di-ether is in the range from 1 to 6 mole % based on the total reaction mixture comprising the olefin, aliphatic carboxylic acid, water, and di-ether*.

2. A process according to claim 1 wherein the amount of water added is in the range from 1 to 7 mole % based on the total of the olefin, aliphatic monocarboxylic acid and water.

3. A process according to claim 1 wherein the amount of water added is in the range from 1 to 5 mole % based on the total of the olefin, aliphatic monocarboxylic acid and water.

4. A process according to claim 1 wherein the heteropolyacid catalyst is supported on a siliceous support which is in the form of extrudates or pellets, said siliceous support having an average pore radius of 30 to 100 Å.

5. A process according to claim 4 wherein the siliceous support is derived from an amorphous, non-porous synthetic silica.

6. A process according to claim 4 wherein the siliceous support is derived from fumed silica produced by flame hydrolysis of $SiCl_4$.

7. A process according to claim 4 wherein the silica support is in the form of pellets or beads or are globular in shape having an average particle diameter in the range from 2 to 10 mm, a pore volume in the range from 0.3–1.2 ml/g, a crush strength of at least 2 Kg force and a bulk density of at least 380 g/l.

8. A process according to claim 4 wherein the siliceous support has at least 99% w/w purity.

9. A process according to claim 4 wherein the siliceous support is a pelleted silica support which has an average bulk density of about 0.39 g/ml, an average pore volume of about 1.15 ml/g and an average particle size ranging from about 0.1–3.5 mm.

10. A process according to claim 9 wherein the pelleted silica support is used as such or after crushing to an average particle size in the range from 0.5–2 mm to support the heteropolyacid catalyst.

11. A process according to claim 1 wherein the heteropolyacids have a molecular weight e.g. in the range from 700–8500 and include dimeric complexes.

12. A process according to claim 4 wherein the amount of heteropolyacid deposited/impregnated on the support for use in the esterification reaction is in the range from 10 to 60% by weight based on the total weight of the heteropolyacid and the support.

13. A process according to claim 1 wherein the olefin reactant used is ethylene, propylene or mixtures thereof.

14. A process according to claim 1 wherein the saturated, lower aliphatic mono-carboxylic acid reactant is a c1–C4 carboxylic acid.

15. A process according to claim 1 wherein the aliphatic mono-carboxylic acid reactant is acetic acid.

16. A process according to claim 1 wherein the reaction mixture has a molar excess of the olefin reactant with respect to the aliphatic mono-carboxylic acid reactant.

17. A process according to claim 1 wherein the mole ratio of olefin to the lower carboxylic acid in the reaction mixture is in the range from 1:1 to 15:1.

18. A process according to claim 1 wherein the mole ratio of olefin to the lower carboxylic acid in the reaction mixture is in the range from 10:1 to 14:1.

19. A process according to claim 1 wherein the reaction is carried out in the vapour phase above the dew point of the reactor contents comprising the reactant acid, any alcohol formed in situ, the product ester and water.

20. A process according to claim 1 wherein the supported heteropolyacid catalyst is used as a fixed bed which is in the form of a packed column.

21. A process according to claim 1 wherein the heteropolyacid catalyst is further modified by the addition of phosphoric acid or other mineral acids thereto.

22. A process according to claim 1 wherein the vapours of the reactant olefins and acids are passed over the catalyst at a GHSV in the range of 100 to 5000 per hour.

23. A process according to claim 1 wherein the esterification reaction is carried out at a temperature in the range from 150°–200° C. using a reaction pressure which is at least 400 KPa.

24. A process according to claim 1 wherein [the reaction mixture is dosed with a] *the* di-ether [which corresponds to the] *comprises a* by-product di-ether formed in situ during the reaction from the reactant olefin [which] *and the* di-ether is recovered and recycled to the reaction mixture.

[25. A process according to claim 24 wherein the amount of di-ether recycled is in the range from 1 to 6 mole percent based on the total reaction mixture comprising the olefin, the aliphatic carboxylic acid, water and di-ether.]

26. A process according claim 24 wherein the di-ether is diethyl ether.

27. A process according to claim 24 wherein the di-ether is an unsymmetrical ether.

* * * * *